United States Patent [19]
Hall et al.

[11] Patent Number: 5,923,044
[45] Date of Patent: Jul. 13, 1999

[54] LITHIUM DIALKYLAMIDE AND LITHIUM ALKYLENECYCLOIMIDE FORMULATIONS AND METHODS OF PREPARATION

[75] Inventors: Randy W. Hall, Kings Mountain; James A. Schwindeman, Lincolnton; Conrad W. Kamienski, Gastonia; John F. Engel, Belmont, all of N.C.

[73] Assignee: FMC Corporation, Philadelphia, Pa.

[21] Appl. No.: 08/856,893

[22] Filed: May 15, 1997

Related U.S. Application Data

[63] Continuation of application No. 08/574,608, Dec. 14, 1995., abandoned

[51] Int. Cl.$^6$ .............................. C09X 3/00; C07C 209/90
[52] U.S. Cl. ............................. 252/182.12; 252/182.14; 564/2; 564/462; 564/463
[58] Field of Search ................. 252/182.12, 182.14; 564/2, 462, 463; 540/400, 484

[56] References Cited

U.S. PATENT DOCUMENTS

| | | | |
|---|---|---|---|
| 4,595,779 | 6/1986 | Morrison et al. | 564/2 |
| 5,002,689 | 3/1991 | Mehta et al. | 252/182.12 |
| 5,149,457 | 9/1992 | Smith | 252/182.12 |
| 5,173,209 | 12/1992 | Smith et al. | 252/182.14 |
| 5,196,138 | 3/1993 | Smith | 252/182.12 |
| 5,300,252 | 4/1994 | Morrison | 252/182.3 |
| 5,391,824 | 2/1995 | Smith | 564/2 |
| 5,493,038 | 2/1996 | Hall et al. | 556/412 |
| 5,574,197 | 11/1996 | Weiss et al. | 585/4 |
| 5,726,308 | 3/1998 | Hall et al. | 540/484 |

FOREIGN PATENT DOCUMENTS

| | | |
|---|---|---|
| 43 32 652 | 9/1993 | Germany . |
| WO 95/23803 | 9/1995 | WIPO . |

OTHER PUBLICATIONS

Reetz, M.T., et al., "Simple Synthesis fo Lithium Diisopropyl amide in Molar Quantities", Liebigs Annalen Der Chemie, vol. 1980, No. 10, pp. 1471–1473, (1980) (untranslated).

Reetz, M.T., et al., "An Economical Large–Scale Synthesis of Titanium Tetrakis(diethylamide) and Chlorotitanium Tris-(Diethylamide)", Synthesis, No. 7, p. 540 (1983).

Primary Examiner—Shean C. Wu
Attorney, Agent, or Firm—Alston & Bird LLP

[57] ABSTRACT

A process for producing nornally liquid hydrocarbon solutions of lithium dialkylamides and lithium alkylenecycloimides, essentially free of ethers and by-product gaseous alkanes derived from C1–C4 alkyllithium compounds, comprising reacting lithium metal with a $C_5$ to $C_{12}$ secondary amine and an electron carrier compound containing at least five carbon atoms in a normally liquid hydrocarbon solvent.

21 Claims, No Drawings

LITHIUM DIALKYLAMIDE AND LITHIUM ALKYLENECYCLOIMIDE FORMULATIONS AND METHODS OF PREPARATION

This application is a continuation of application Ser. No. 08/574,608, filed Dec. 14, 1995, now abandoned.

FIELD OF THE INVENTION

The present invention concerns novel lithium dialkylamide and lithium alkylenecycloimide compositions, their stable solutions in normally liquid hydrocarbon solvents, and improved methods for their production.

BACKGROUND OF THE INVENTION

The bulky organoamides of alkali metals are used extensively as reagents in organic synthesis by virtue of the combination of their strong Bronsted basicity and their low nucleophilicity. Lithium dialkylamide and lithium alkylenecycloimide compounds such as lithium diisopropylamide (LDA), lithium hexamethyldisilazide (LHS) and lithium pyrrolidide (LPA), and are essentially insoluble in Lewis base-free hydrocarbon solvents. Although these compounds are soluble in ethers, they are quite unstable with time even at room temperature (except for LHS). Their stability can be improved by dissolving them in hydrocarbon solvents containing limited amounts of Lewis bases and further, by addition of small amounts of magnesium dialkylamides to these solutions.

The above described solutions may be prepared by reaction of the appropriate secondary amine in the desired solvent combination with either an alkyllithium, such as, e.g., n-butyllithium, or with lithium metal in the presence of an electron carrier, such as isoprene or styrene. In the latter case Lewis bases such as ethyl ether or tetrahydrofuran have been taught to be necessary for the metal reactions to proceed.

Recently, it was shown in U.S. Pat. No. 5,149,457 (EPO 423 087, 406,197) that certain secondary amines, such as, e.g., diisobutylamine, can be reacted with alkyllithium reagents such as, e.g., n-butyllithium, in purely hydrocarbon solvents to yield stable solutions of the corresponding lithium dialkylamide. However, these solutions contain the gaseous hydrocarbon by-products of the reaction, e.g., n-butane. These are not desirable because they increase the flammability of the product solutions and cause problems in subsequent solvent recycle. In addition, the process requires the use of the expensive organometallic reagent (viz., n-butyllithium).

SUMMARY OF THE INVENTION

The present invention provides a process for producing normally liquid hydrocarbon solutions of lithium dialkylamides and lithium alkylenecycloimides, essentially free of ethers and by-product gaseous alkanes derived from C1–C4 alkyllithium compounds, whereby lithium metal is reacted with a secondary amine and an electron carrier compound, other than 1,3-butadiene, in a normally liquid hydrocarbon solvent. The products of the process are liquid solutions of either lithium dialkylamides such as lithium diisobutylamide and lithium alkylenecyclocycloimides such as lithium hexamethyleneimide in a liquid hydrocarbon solvent, free of by-product gaseous alkanes derived from C1–C4 alkyllithium compounds, using lithium metal and an electron carrier compound, other than 1,3-butadiene, without the need for any added Lewis base compounds such as tetrahydrofuran. Even lithium dialkylamides possessing a very low solubility in hydrocarbon solvents, such as, e.g., lithium diisopropylamide, can be prepared in this manner in a hydrocarbon solvent in the absence of tetrahydrofuran, although thick, intractable solutions are produced thereby. On the other hand, when hexamethyleneimine is mixed with lithium metal in tetrahydrofuran or in mixtures of tetrahydrofuran and normally liquid hydrocarbons in the absence of an electron carrier the reactions proceed slowly, even at reflux. Thus, the key operative component in these metal-dialkylamine reactions is the electron carrier, and not the Lewis base.

It is thus an advantage of this invention to employ a process to produce lithium diisobutylamide, lithium hexamethyleneimide and other highly hydrocarbon-soluble lithium dialkylamides and lithium alkylenecycloimides directly in normally liquid hydrocarbon solvents using the less expensive (than n-butyllithium) lithium metal in the absence of relatively expensive Lewis bases, such as, e.g., ethers like tetrahydrofuran, which heretofore have been taught to be necessary for this reaction to proceed.

It is another advantage of this invention to produce these lithium dialkylamides and lithium alkylenecycloimides in normally liquid hydrocarbon solvents without a concomitant gaseous byproduct hydrocarbon impurity.

DESCRIPTION OF THE PREFERRED EMBODIMENTS

According to a preferred method of the present invention, lithium dialkylamides or lithium alkylenecycloimides are produced directly from lithium metal, in the form of finely dispersed particles (less than 100 microns), containing at least 0.1 percent sodium, suspended in a normally liquid hydrocarbon solvent such as cyclohexane or a hydrocarbon selected from $C_5$–$C_{12}$ aliphatic hydrocarbons, $C_6$–$C_{76}$ cycloaliphatic hydrocarbons and $C_6$–$C_{16}$ aromatic hydrocarbons and mixtures thereof, and a secondary amine, such as diisobutylamine or hexamethyleneimine, and half an equivalent of an electron carrier such as styrene at an elevated temperature, such as about 50 degrees centigrade for a suitable reaction period. Reacting diisobutylamine with lithium metal dispersed in cyclohexane, a preferred hydrocarbon solvent, at a reaction temperaure of about 50° C., for a reaction period of about four hours, produced a solution of lithium diisobutylamide in cyclohexane in a yield of about 89 percent. Similarly, lithium metal was reacted with hexamethyleneimine and styrene at 50 degrees centigrade over a four hour period to give a 1.65 molar solution of lithium hexamethyleneimide in cyclohexane in a yield of about 88 percent. The resulting product solutions contained no gaseous by-products. The by-product residue resulting from the reaction of the electron carrier compound styrene with lithium metal and secondary amine is the normally liquid hydrocarbon compound ethylbenzene (boiling point=135 degrees centigrade). When isoprene is used as the electron carrier compound, instead of styrene, the by-product resulting from the reaction with lithium and secondary amine is the normally liquid hydrocarbon 2-methyl-2-butene (boiling point=31–32° Centigrade).

Typical secondary amines, which, on lithiation result in fluid, normally liquid hydrocarbon solutions of lithium dialkylamides or lithium alkylenecycloimides, include but are not limited to diisobutylamine, di-sec-butylamine, diisopentylamine, hexamethyleneimine, 2-methylpiperidine, 2,6-dimethylpiperidine, 2,2,6,6-tetramethylpiperidine and other amines listed in U.S. Pat.

No. 5,149,457 and in EP applications 0593,049, 0594,107 and 0590,491 hereby incorporated by reference, can be used in the process of this invention to produce the desired products of this invention.

Electron carrier compounds typically employed to promote reactions between lithium metal and the secondary amine are conjugated 1,3-dienes which include but are not limited to isoprene, 1,3-pentadiene, 4-methyl-1,3-pentadiene, 2,4-dimethyl-3-isopropyl-1,3-pentadiene (1,3-butadiene is not used in the present invention) and vinylaromatic compounds such as styrene, divinylbenzene and napthalene. Generally, the ratio of secondary amine to electron carrier used is two.

Solvents which can be employed to produce the products of this invention are normally liquid $C_5$–$C_{12}$ aliphatic hydrocarbons, $C_6$–$C_{16}$ cycloaliphatic hydrocarbons and $C_6$–$C_{16}$ aromatic hydrocarbons and mixtures thereof and include but are not limited to hydrocarbons such as pentane, hexane, heptane, cyclohexane, methylcyclohexane, benzene, toluene, ethylbenzene and the xylenes. For higher concentrations of the desired lithium dialkylamides and lithium alkylene cycloimides it is preferable to employ the cycloaliphatic and aromatic hydrocarbons, such as cyclohexane and toluene.

Reaction temperatures employed in the process of this invention can be varied broadly, although they are, of course, dependent on the stability of the desired lithium dialkylamide or lithium alkylenecycloimide. Generally, the reaction temperature range can be varied between about 35 degrees centigrade to the reflux temperature of the solvent employed. However, a more preferred range is from about 40–60 degrees centigrade.

The concentration range of the desired lithium dialkylamides and lithium alkylenecycloimides as produced in the process of the invention can be varied from about 1–3 moles per liter of solution but will, of course, depend on the solubility of the product in the liquid hydrocarbon employed.

The reactions may be carried out at ordinary (atmospheric) pressure, but the atmospheric composition above the contents of the reaction vessel should be inert. Thus, the atmosphere should be dry and inert to lithium metal, i.e., most favorably be argon gas.

The following examples further illustrate the invention.

EXAMPLE 1

Synthesis of Lithium Hexamethyleneimide in Cyclohexane Employing Styrene (No THF) (9626)

A reactor equipped with a reflux condenser, a temperature indicating device, an addition funnel for adding liquid materials to the reactor, an external heating mantle, a source of argon for maintaining an inert atmosphere and a mechanical stirrer was charged with 15.94 grams (2.29 moles) of lithium metal in the form of dry lithium powder which was obtained by washing and drying a lithium metal dispersion, 150 milliters of dry cyclohexane, 38.8 grams of coarse sand and 87.08 grams (0.878 moles) of hexamethyleneimine. In the addition funnel were placed 37.6 grams of styrene (0.361 moles) and 50 milliliters of dry cyclohexane. The reactor and contents were heated with the heating mantle to 50.4 degrees C and the reaction mass was moderately stirred throughout styrene addition and post reaction times.

Addition of the styrene brought about an immediate exotherm of about 3 degrees C in 1 minute indicating initiation of reaction. The remaining styrene was added dropwise to the reactor over a period of 65 minutes. The reaction temperature was maintained at about 48 degrees C throughout the styrene addition period. The reaction mass was stirred and heated to about 50 degrees C during an additional 60 minutes of post reaction time. It was then cooled and pressure filtered to yield a golden yellow solution of lithium hexamethyleneimide in cyclohexane.

A total weigh of 316 grams of a 1.65 M solution of lithium hexamethyleneimide was obtained. The recovered yield was 88 percent. Three weeks after placing the filtered solution in the refrigerator at about 0 degrees C no precipitation of product had occurred.

EXAMPLE 2

Synthesis of Lithium Diisobutylamide in Cyclohexane Employing Styrene (No THF) (9711)

To a reactor equipped as in example 1 was charged 4.85 grams (0.699 moles) of lithium metal in the form of dry lithium powder which was obtained by washing and drying a lithium metal dispersion, 250 milliliters of dry cyclohexane, and 51.4 grams (0.398 moles) of diisobutylamine. In the addition funnel were placed 20.24 grams of styrene (0.194 moles) and 63 milliliters of dry cyclohexane. The reactor and contents were heated with the heating mantle to 48.2 degrees C and the reaction mass was moderately stirred throughout styrene addition and post reaction times.

Addition of the styrene brought about an immediate exotherm of about 3 degrees C in 10 minutes indicating initiation of reaction. The remaining styrene was added dropwise to the reactor over a period of 43 minutes. The reaction temperature was maintained at about 50 degrees C throughout the styrene addition period. The reaction mass was stirred and heated to about 50 degrees C during an additional 60 minutes of post reaction time. It was then cooled and pressure filtered to yield a dark peach solution of lithium diisobutylamide in cyclohexane.

A total weigh of 363.7 grams of a 0.75 M solution of lithium diisobutylamide was obtained. The recovered yield was 89 percent.

EXAMPLE 3

Preparation of Lithium Diisopropylamide in Ethylbenzene (No THF) (10072)

A weight of 7.61 grams (1.096 moles) of lithium powder was suspended in 110 milliliters of ethylbenzene and 85.4 grams (0.8439 moles) of diisopropylamine and the mixture heated at 50 to 53 degrees Centigrade while a mixture of 44.7 grams (0.429 moles) of styrene in 75 milliliters of ethylbenzene was added dropwise. Reaction occurred immediately as indicated by a rise in temperature. After 59 milliliters (53.5% of the total feed) of the solution in the dropping funnel had been added the mixture became so thick that it could no longer be stirred. The feed was discontinued and the mixture heated to 90 degrees Centigrade, but stirring was still slow. The mixture was allowed to cool to room temperature. Four increments of tetrahydrofuran were added (a total of 0.478 moles) in a 10 minute period before the mixture thinned out sufficiently to be stirrable. The mixture was filtered and the solids washed twice with 25 milliliters of ethylbenzene. A total of 301 grams of solution was obtained. The solution contained a total of 0.459 moles of lithium diisopropylamide as determined by a modified Watson-Eastham titration. Based on the total moles of styrene added the yield of product was 99%.

COMPARATIVE EXAMPLE

Preparation of Lithium Hexamethyleneimide in Cyclohexane Containing One Equivalent of Tetrahydrofuran (No Electron Carrier) (10079)

To a stirred mixture of 2.97 grams (0.428 moles) of lithium powder, 17.81 grams (0.2469 moles) of tetrahydrofuran and 125 milliliters of cyclohexane was quickly added 23.65 grams (0.2384 moles) of hexamethyleneimine at 50 degrees Centigrade. No exotherm was noted. After continued heating for 2 hours, analysis of the solution showed that only a 4% conversion to product had occurred. Further heating at reflux for 1.5 hours increased the conversion to only 14%. After a further 2 hours at reflux the yield was still only 26%. The reaction was discontinued.

No studies of stability of any of the solutions was carried out.

We claim:

1. Liquid hydrocarbon solutions, essentially free of ethers and gaseous $C_1$ to $C_4$ alkanes, consisting essentially of substantially hydrocarbon soluble lithium $C_5$ to $C_{12}$ dialkylamides or lithium $C_5$ to $C_{12}$ alkylenecycloimides, with the proviso that said lithium $C_5$ to $C_{12}$ dialkylamide is not lithium diisopropylamide (LDA), a hydrocarbon selected from the group consisting of $C_5$ to $C_{12}$ aliphatic hydrocarbons, $C_6$ to $C_{16}$ cycloaliphatic hydrocarbons and $C_6$ to $C_{16}$ aromatic hydrocarbons and a liquid electron carrier residue, wherein said liquid hydrocarbon solution is essentially free of ethers and gaseous $C_1$ to $C_4$ alkanes.

2. The liquid hydrocarbon solutions of claim 1 in which the lithium dialkylamide is lithium diisobutylamide and the lithium alkylene-cycloimide is lithium hexamethyleneimide.

3. The liquid hydrocarbon solutions of claim 1 in which the liquid hydrocarbon solvent is cyclohexane.

4. The liquid hydrocarbon solution of claim 1 in which the electron carrier compound residue is ethylbenzene.

5. The liquid hydrocarbon solution of claim 1 in which the electron carrier residue compound is 2-methyl-2-butene.

6. The liquid hydrocarbon solution of claim 1, wherein said $C_5$ to $C_{12}$ dialkylamide is selected from the group consisting of lithium diisobutylamide, lithium di-sec-butylamide, and lithium diisopentylamide.

7. The liquid hydrocarbon solution of claim 1, wherein said lithium $C_5$ to $C_{12}$ alkylenecycloimide is selected from the group consisting of lithium hexamethyleneimide, lithium 2-methylpiperidide, 2,6-dimethylpiperidide, and 2,2,6,6-tetramethylpiperidide.

8. The liquid hydrocarbon solution of claim 1, wherein said hydrocarbon is selected from the group consisting of pentane, hexane, heptane, cyclohexane, methylcyclohexane, benzene, toluene, ethylbenzene, and xylene.

9. The liquid hydrocarbon solution of claim 1, wherein said electron carrier residue is the residue of an electron carrier compound selected from the group consisting of isoprene, 1,3-pentadiene, 4-methyl-1,3-pentadiene, 2,4-dimethyl-3-isopropyl-1,3-pentadiene, styrene, divinylbenzene and naphthalene.

10. A liquid hydrocarbon solution, essentially free of ethers and gaseous $C_1$ to $C_4$ alkanes, consisting essentially of lithium diisobutylamide or lithium hexamethyleneimide, a hydrocarbon selected from the group consisting of $C_5$–$C_{12}$ aliphatic hydrocarbons, $C_6$–$C_{16}$ cycloaliphatic hydrocarbons and $C_6$–$C_{16}$ aromatic hydrocarbons and an electron carrier residue, wherein said liquid hydrocarbon solution is essentially free of ethers and gaseous $C_1$ to $C_4$ alkanes.

11. The liquid hydrocarbon solution of claim 10 in which the liquid hydrocarbon solvent is cyclohexane.

12. The liquid hydrocarbon solution of claim 10 in which the electron carrier compound residue is ethylbenzene.

13. The liquid hydrocarbon solution of claim 10 in which the electron carrier residue compound is 2-methyl-2-butene.

14. The liquid hydrocarbon solution of claim 10, wherein said hydrocarbon is selected from the group consisting of pentane, hexane, heptane, cyclohexane, methylcyclohexane, benzene, toluene, ethylbenzene, and xylene.

15. The liquid hydrocarbon solution of claim 10, wherein said electron carrier residue is the residue of an electron carrier compound selected from the group consisting of isoprene, 1,3-pentadiene, 4-methyl-1,3-pentadiene, 2,4-dimethyl-3-isopropyl-1,3-pentadiene, styrene, divinylbenzene and naphthalene.

16. A liquid hydrocarbon solution, essentially free of ethers and gaseous $C_1$–$C_4$ alkanes, consisting essentially of lithium $C_5$–$C_{12}$ alkylenecycloimides, a hydrocarbon selected from the group consisting of $C_5$–$C_{12}$ aliphatic hydrocarbons, $C_6$–$C_{16}$ cycloaliphatic hydrocarbons and $C_6$–$C_{16}$ aromatic hydrocarbons and an electron carrier residue, wherein said liquid hydrocarbon solution is essentially free of ethers and gaseous $C_1$ to $C_4$ alkanes.

17. The hydrocarbon solution of claim 16 in which the lithium alkylenecycloimide is lithium hexamethyleneimide.

18. The liquid hydrocarbon solution of claim 16, wherein said lithium $C_5$ to $C_{12}$ alkylenecycloimide is selected from the group consisting of lithium hexamethyleneimide, lithium 2-methylpiperidide, 2,6-dimethylpiperidide, and 2,2,6,6-tetramethylpiperidide.

19. The liquid hydrocarbon solution of claim 16, wherein said hydrocarbon is selected from the group consisting of pentane, hexane, heptane, cyclohexane, methylcyclohexane, benzene, toluene, ethylbenzene, and xylene.

20. The liquid hydrocarbon solution of claim 16, wherein said electron carrier residue is the residue of an electron carrier compound selected from the group consisting of isoprene, 1,3-pentadiene, 4-methyl-1,3-pentadiene, 2,4-dimethyl-3-isopropyl-1,3-pentadiene, styrene, divinylbenzene and naphthalene.

21. A liquid hydrocarbon solution, essentially free of ethers and gaseous $C_1$ to $C_4$ alkanes, consisting essentially of lithium diisobutylamide or lithium hexamethyleneimide, cyclohexane, and an electron carrier residue selected from the group consisting of ethylbenzene and 2-methyl-2-butene, wherein said liquid hydrocarbon solution is essentially free of ethers and gaseous $C_1$ to $C_4$ alkanes.

* * * * *